US012709632B2

(12) United States Patent
Pearson et al.

(10) Patent No.: US 12,709,632 B2
(45) Date of Patent: Aug. 18, 2026

(54) METHODS FOR HARVESTING BIOMOLECULES

(71) Applicant: AMGEN INC., Thousand Oaks, CA (US)

(72) Inventors: Thomas Clark Pearson, Newbury Park, CA (US); Sarah Whetstone, Thousand Oaks, CA (US); Jeremy S. Conner, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 1059 days.

(21) Appl. No.: 17/794,889

(22) PCT Filed: Jan. 22, 2021

(86) PCT No.: PCT/US2021/014761
§ 371 (c)(1),
(2) Date: Jul. 22, 2022

(87) PCT Pub. No.: WO2021/150996
PCT Pub. Date: Jul. 29, 2021

(65) Prior Publication Data

US 2023/0058276 A1 Feb. 23, 2023

Related U.S. Application Data

(60) Provisional application No. 62/965,537, filed on Jan. 24, 2020.

(51) Int. Cl.
*C07K 1/36* (2006.01)
*C07K 1/34* (2006.01)
*C12M 1/26* (2006.01)

(52) U.S. Cl.
CPC .................. *C07K 1/36* (2013.01); *C07K 1/34* (2013.01); *C12M 33/10* (2013.01)

(58) Field of Classification Search
CPC ... C07K 1/36; C07K 1/34; C07K 1/14; C12M 33/10
See application file for complete search history.

(56) References Cited

U.S. PATENT DOCUMENTS

| | | | | |
|---|---|---|---|---|
| 6,319,494 | B1 | 11/2001 | Capon et al. | |
| 7,741,465 | B1 | 6/2010 | Eshhar et al. | |
| 10,533,045 | B2 * | 1/2020 | Allison | C07K 1/165 |
| 2004/0265470 | A1 | 12/2004 | Ciantar et al. | |
| 2005/0037333 | A1 * | 2/2005 | Pham | C12M 47/02 435/358 |

FOREIGN PATENT DOCUMENTS

| | | | | | |
|---|---|---|---|---|---|
| WO | 03/13267 | A1 | 2/2003 | | |
| WO | 2014/145744 | A1 | 9/2014 | | |
| WO | 2014/180577 | A1 | 11/2014 | | |
| WO | 2016/197057 | A1 | 12/2016 | | |
| WO | WO-2019197292 | A1 * | 10/2019 | | A23J 3/08 |

OTHER PUBLICATIONS

Bielser et al., Continuous bleed recycling significantly increases recombinant protein production yield in perfusion cell cultures, Biochemical Engineering Journal, vol. 169, 2021, 107966 (Year: 2021).*
Haeberle et al. Centrifugal extraction of plasma from whole blood on a rotating disk, Lab Chip, 2006, vol. 6, p. 776-781 (Year: 2006).*
Richardson et al. Continuous Solids-Discharging Centrifugation. A Solution to the Challenges of Clarifying High-Cell-Density Mammalian Cell Cultures, BioProcess Int., Apr. 2018 (Year: 2018).*
Yang et al. Perfusion seed cultures improve biopharmaceutical fed-batch production capacity and product quality. Biotechnol Progress, 30: 616-625 (Year: 2014).*
Bielser Development of perfusion cell culture processes for the manufacturing of therapeutic recombinant proteins retrieved from <www.research-collection.ethz.ch/server/api/core/bitstreams/21dc644c-a6c4-4079-817c-bafb502c16b0/content> on Mar. 13, 2026 (Year: 2019).*
Searles et al. Viable cell recycle with an inclined settler in the perfusion culture of suspended recombinant Chinese hamster ovary cells. Biotechnol Prog. Mar.-Apr. 1994;10(2):198-206 (Year: 1994).*
Genck et al., Perry's Chemical Engineers' Handbook, 8th ed. McGraw-Hill Co., Inc., (2008).
International Application No. PCT/US2021/014761, International Preliminary Report on Patentability, mailed Aug. 4, 2022.
International Application No. PCT/US2021/014761, International Search Report and Written Opinion, mailed May 31, 2021.

* cited by examiner

*Primary Examiner* — Joanne Hama
*Assistant Examiner* — Emmanuel Led Youtchom Pendie
(74) *Attorney, Agent, or Firm* — Lauren Mangano Drenkard

(57) ABSTRACT

The disclosure provides methods of purifying native and recombinant biomolecules, e.g., proteins, from mammalian cells using purification protocols incorporating harvest recovery operations involving decanter centrifugation of at least one target biomolecule from at least one particulate component of cell culture fluid. The unexpected capacity of decanter centrifuge separation of biological materials of similar densities found in mammalian cell culture fluid has been found to yield high quantities of functional protein in efficient, low-cost harvest recovery steps of biomolecule purification protocols.

17 Claims, 3 Drawing Sheets

A
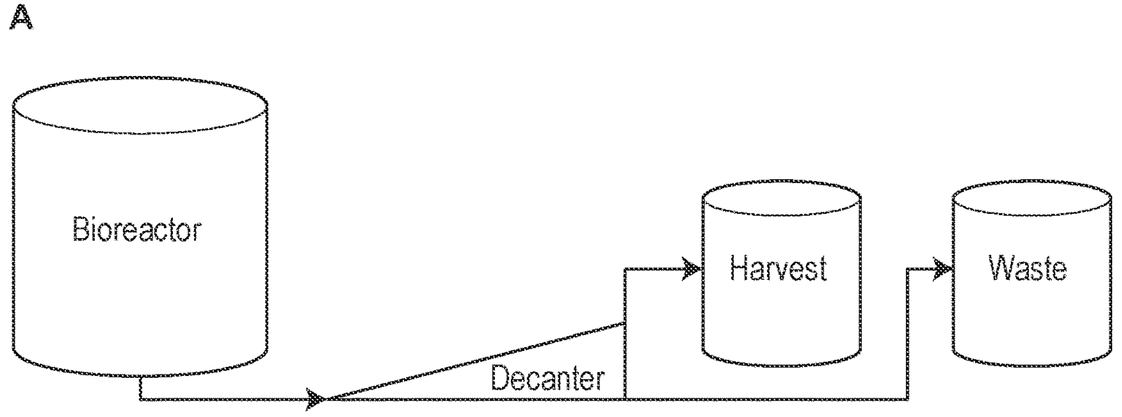
B
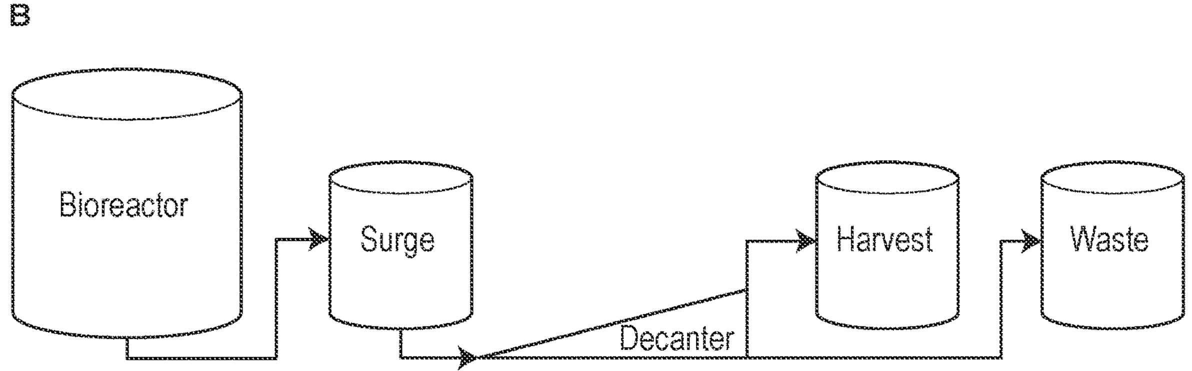
Figure 1 (1/2)

C
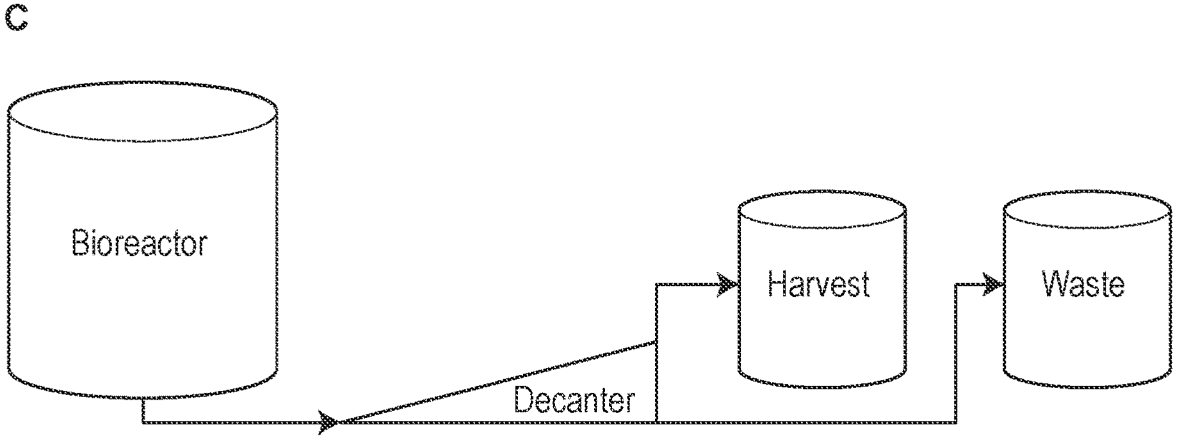
D
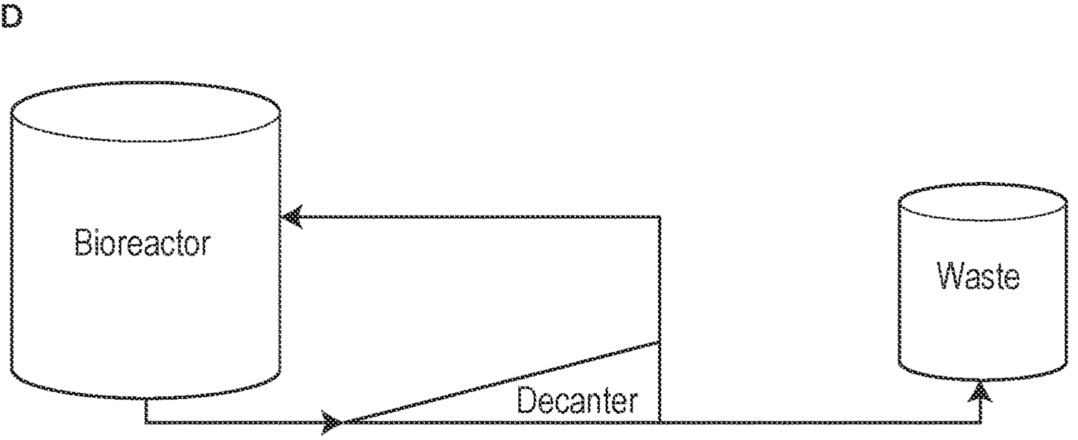
Figure 1 (2/2)

METHODS FOR HARVESTING BIOMOLECULES

CROSS-REFERENCE TO RELATED APPLICATIONS

This is a U.S. National Phase of International Application PCT/US2021/014761, filed Jan. 22, 2021, which claims priority to U.S. Patent Application No. 62/965,537, filed Jan. 24, 2020, which are incorporated herein by reference in their entirety.

FIELD

The disclosure generally relates to the field of biomolecular processing, and more particularly to the field of harvesting biomolecules from compositions such as mammalian cell cultures.

BACKGROUND

Modern medicine faces many challenges in its effort to treat, if not cure, a wide variety of diseases and conditions afflicting humans and other animal species. The effort to develop new and better treatments and cures extends to efforts to develop new and better pharmaceuticals, including macromolecular biological compounds or biologics, such as monoclonal antibodies (mAbs). In recent years, those efforts have borne fruit at a steady pace, with an ever-increasing group of therapeutically active mAbs approved for use in humans and filling the pipelines of pharmaceutical firms. A natural adjunct to the effort to develop new therapeutics is the effort to improve antibody production processes by increasing the yield of intact, functional antibody while reducing the cost of that production, at all levels of production, i.e., laboratory- or research-, pilot-, and commercial-scale production levels.

Antibodies are typically produced by expression in cell culture, often involving mammalian cell culture. Antibody production processes generally involve several steps, beginning with a harvest recovery step in which a desired or target antibody is separated from other components of cell culture, including intact cells, cell debris, non-target host cell protein, DNA and other nucleic acids, lipids, carbohydrates, and viral particles. Following the harvest recovery step, processes typically involve a target capture step, e.g., a protein A-based capture for antibodies, with subsequent chromatography steps to refine or polish the purification of the target antibody.

While efforts continue to improve all stages of the process of purifying macromolecular biologics like antibodies, recent improvements in both engineering host cells and in cell culture techniques has led to dramatic increases in the cell densities of cultures used in the manufacture of biologics. With the engineering of PER.C6 cells, and even with CHO cell cultures, cell densities that were on the order of $10^6$ cell/ml a few years ago can now reach into the $10^8$ cells/ml range. The apparent benefits of producing more with less by increasing the density of the cell factories expressing the target biologic provide strong incentives for continuing to develop purification processes capable of handling high cell-density cultures for the production of biologics in batch, perfusion-batch and continuous production modes.

The shift towards higher cell density cultures for antibody production processes has placed pressure on efforts to improve the initial step of harvest recovery, where target antibodies are separated from other culture components. Traditional harvest recovery steps relied on centrifugation, filtration, or a combination of these techniques. Disk-stack centrifugation has become a common component of harvest recovery operations because it is capable of handling a continuous flow of cell culture fluid as well as the periodic deliveries from batch culture operations. Disk-stack centrifugation can separate fluids containing a target biologic from solids resulting from cell culture, but there is a limit. Disk-stack centrifuges have a lower bound on the size of particles that can be efficiently separated from culture fluids, and that limit is too high to capture all host cell proteins and nucleic acids such as DNA. Moreover, as the cell density of cultures increases, the limitations of disk-stack centrifugation become apparent as the centrifuge clogs more rapidly due to the higher solids burden in the cell culture fluid. If clogging is addressed by discharging solids from the centrifuge more frequently, target is also lost, reducing the yield. Thus, disk-stack centrifugation is often coupled with another primary separation technique such as filtration or the size of culture particles are altered to accommodate the limitations of disk-stack centrifugation, for example by creating larger particles through flocculation or precipitation.

Filtration has been considered as a sole primary separation technique and as a partner to centrifugation, e.g., disk-stack centrifugation, to separate target biologics from other cell culture components released from bioreactors housing cell cultures used for the production of biologics. Depth filters have become established as one of the main techniques routinely employed in existing harvest recovery steps. Depth filters generally are thick filters composed of cellulosic or synthetic fibers creating a three-dimensional network of pores that collectively establish tortuous paths that materials must take to pass through the filter. Larger particulate matter from cell cultures, e.g., cells, cell debris, some flocculated materials, rapidly foul filters by plugging the pores, leading to the adoption of tangential flow microfiltration in which the direction of cell culture fluid flow is tangential to the direction of migration through the depth filter. In this manner, the larger particles move across the surface of the filter and are returned to the bioreactor rather than settling into and clogging the pores of the filter. Further improvement has been achieved by the use of alternative tangential flow microfiltration in which the direction of cell culture fluid across the surface of the membrane is periodically reversed, thereby providing a flushing action. The motivation to develop alternative tangential flow microfiltration highlights the fact that particulate matter in cell culture fluid tends to clog filters, and adopting alternative tangential flow microfiltration is an incomplete solution to that problem. The increasing density of cell cultures now being used to produce biologics has resulted in pressure to increase the surface are of depth filters to accommodate the increased solids load, and this increases costs for materials and labor.

One approach to address the limitations of disk-stack centrifugation has been to introduce a flocculation or precipitation step in the harvest recovery operation. Flocculated or precipitated materials have larger average particle sizes than the native materials, resulting in more efficient separation from the fluid containing the target biologic in a disk-stack centrifugation run. This results in improved performance of disk-stack centrifugation separation, and also facilitates further clarification by depth filtration following such centrifugation runs due to the lowered levels of small particulates that would otherwise participate in pore-clogging. While introducing a flocculation/precipitation improves the performance of disk-stack centrifugation and depth filtration, it does come at the cost of introducing another step in the biologic production process, involving the cost of the flocculant/precipitant and additional labor. In addition, there is the challenge, and cost, of removing the flocculant/precipitant, some of which can be toxic at relatively low residual levels.

Another approach to the limitations of existing harvest recovery operations is to avoid the use of centrifugation altogether. Acoustic wave separation is a technique for separating cell culture fluid containing a target biologic from the solids contained in untreated cell culture fluid. The technique relies on flowing cell culture fluid through a channel subjected to acoustic forces oriented to create a three-dimensional standing acoustic wave having nodes in that channel. Solids become trapped in the nodes while the fluid containing the target passes through. The trapped solids aggregate, leading to their eventual settling out of the fluid. The technique is gentle and shows some promise, but currently it is not capable of achieving sufficient clarification and is used in conjunction with depth filtration. Like other conventional techniques, acoustic wave separation also struggles to clarify cell culture fluids from culture of high density cells, leading to the need to incorporate additional acoustic wave separation units, at increased cost.

For the foregoing reasons, a need persists in the art for biomolecule (e.g., biologic) purification processes involving a harvest recovery step that efficiently and cost-effectively results in high yield separations of biologics such as antibodies from other cell culture components arising from high-cell-density cell culturing.

SUMMARY

The disclosure provides methods for harvesting proteins from mammalian cells that are versatile in providing for the harvest of proteins from high-density mammalian cell cultures as well as lower density mammalian cell cultures. The protein harvest methods incorporate the unconventional approach of using a decanter centrifuge rather than the conventional disk-stack centrifuge. As noted herein, developments in the harvest recovery step of processing target biologics (e.g., monoclonal antibodies) produced in cell culture have focused on adding steps to aid disk-stack centrifugation by flocculating/precipitating cell culture solids or by further clarifying cell culture fluid after disk-stack centrifugation by using depth filters. Other advances in harvest recovery have substituted acoustic wave separation for disk-stack centrifugation in an attempt to achieve the separation of target biologics from cell culture solids without the limitations imposed by disk-stack centrifugation. Based on the existing knowledge in the art, decanter centrifugation has not been contemplated for use in the harvest recovery of target biologics from mammalian cell culture fluid because the state of the art held the view that a limitation of decanter centrifuges was that they could not separate biological solids with small density differences, such as cells and viruses. Genck et al., Perry's Chemical Engineers' Handbook ($8^{th}$ ed. McGraw-Hill Co., Inc.) 2008. The disclosure provides methods based on the surprising realization that decanter centrifuges are effective in separating these biological solids with small density differences, and the use of a decanter centrifuge as a central component of the harvest recovery step of biologic production processes provides an efficient and cost-effective approach to the purification of a wide range of biologics, including antibodies such as monoclonal antibodies.

These biologic production processes provide high yields of functional biologics using approaches that, in addition to a primary separation using a decanter centrifuge, are also compatible with, and can therefore include, other known harvest recovery technologies such as flocculation, precipitation, depth filtration (e.g., tangential flow microfiltration, alternative tangential flow microfiltration), and even acoustic wave separation. Beyond the harvest recover step, the disclosure comprehends methods involving all known post-harvest recovery technologies, such as protein A purification of immunoglobulin and immunoglobulin-like biologics as well as chromatography-based separations and polishing steps that include column and alternative modes of chromatographic separations by ion exchange chromatography (IEX), including anion exchange chromatography (AEX) and/or cation exchange chromatography (CEX), hydrophobic interaction chromatography (HIC), mixed modal or multimodal chromatography (MM), hydroxyapatite chromatography (HA), reverse-phase chromatography, size exclusion chromatography (SEC), gel filtration, or any other known form of chromatographic separation of biological and/or biochemical substances.

The disclosure makes use of at least one decanter centrifuge to enable longer term continuous harvest of mammalian cell culture. Use of a decanter centrifuge enables a clear flow path and minimizes fouling concerns for any subsequent downstream filtration process by providing an effective initial separation of the recombinant proteins from heavier culture components, such as cells, cell debris, aggregated proteins, and the like, with the ability to harvest higher density cells and the potential to recover a significant additional portion of a cell culture harvest that has been lost using other harvest methods. The methods according to the disclosure are also suitable for use in fed-batch culturing of mammalian cells expressing target biologic.

In one aspect the disclosure provides a method for separating protein produced in a mammalian cell from at least one other mammalian cell component comprising: (a) introducing a fluid comprising mammalian cells into at least one decanter centrifuge; (b) operating the decanter centrifuge, thereby separating fluid components into a low density composition and a high density composition; (c) collecting the low density composition or recycling the low density composition through the decanter centrifuge; and (d) recycling the high density composition through the decanter centrifuge or passing the high density composition to waste, wherein the fluid components comprise mammalian cells and components of mammalian cells, further wherein the low density composition comprises the protein. In some embodiments, the fluid comprising mammalian cells is a culture harvest from a bioreactor comprising cultured mammalian cells. In some embodiments, a continuous stream of culture harvest is introduced into at least one decanter centrifuge. In some embodiments, a discontinuous batch of culture harvest is introduced into at least one decanter centrifuge. In some embodiments, the at least one decanter centrifuge is a plurality of decanter centrifuges. In some embodiments, the plurality of decanter centrifuges is two decanter centrifuges. In some embodiments, the high density composition is recycled through the decanter centrifuge. In some embodiments, the low density composition is recycled through the decanter centrifuge. In some embodiments, the high density composition and the low density composition are recycled through the decanter centrifuge. In some embodiments, the low density composition is recycled at least one time through a bioreactor comprising a culture of the mammalian cells. In some embodiments, the low density composition is recycled into the bioreactor while the high density composition is passed to waste.

The methods according to the disclosure further comprehend some embodiments in which the protein is a synthetic protein. In some embodiments, the protein is a recombinant protein. In some embodiments, the recombinant protein is a eukaryotic protein, such as a mammalian protein. In some embodiments, the mammalian protein is an antibody chain or an antigen-binding fragment thereof. In some embodiments, the mammalian protein is an antigen-binding protein, such as an antibody, a peptibody, an antibody fragment, an antibody derivative, an antibody analog, a fusion protein, a mutein, a bispecific protein or a multispecific protein. In some embodiments, the antibody is a whole antibody, a single-chain variable fragment, a Fv, a Fab, a Fab', a F(ab')2, a diabody, a triabody, a tetrabody, a BiTE, a Fd, a dAb, a minibody, or a maxibody. In some embodiments, the protein is a chimera. In some embodiments, the chimera comprises an antibody chain or an antigen-binding fragment thereof comprising light chain complementarity determining regions 1, 2 and 3 or heavy chain complementarity determining regions 1, 2 and 3. In some embodiments, the chimera is a Chimeric Antigen Receptor (CAR).

Further contemplated are embodiments in which the protein is a granulocyte colony-stimulating factor, an erythropoiesis stimulating agent, a HER receptor, a cell adhesion molecule, a growth factor, an osteoinductive factor, insulin, a coagulation protein, a colony stimulating factor, a blood group antigen; a growth hormone, a growth hormone receptor, a T-cell receptor; a neurotrophic factor, a neurotrophin, a relaxin, an interferon, an interleukin, a viral antigen, a lipoprotein, an integrin, a rheumatoid factor, an immunotoxin, a surface-membrane protein, a transport protein, a homing receptor, an addressin, a regulatory protein, or an immunoadhesin. In some embodiments, the growth factor is a nerve growth factor, a fibroblast growth factor, a transforming growth factor, or an insulin-like growth factor. In some embodiments, the method further comprises subjecting the low density composition to a second centrifugation step, such as wherein the second centrifuge is a disk-stack centrifuge. In some embodiments, the method further comprises subjecting the low density composition to a filtration step, such as depth filtration or tangential flow filtration. In some embodiments, the method further comprises subjecting the cell culture or the low density composition to acoustic wave separation. In some embodiments, the method further comprises subjecting the low density composition to a flocculation step or a precipitation step. In some embodiments, the method further comprises subjecting the low density composition to any one or more of a second centrifugation step, a filtration step, an acoustic wave separation step, a flocculation step or a precipitation step.

Another aspect of the disclosure is directed to a method for purifying a protein from a mammalian cell culture comprising: (a) introducing a cell culture fluid comprising mammalian cells into at least one decanter centrifuge; (b) operating the decanter centrifuge, thereby separating fluid components into a low density fluid composition and a high density fluid composition; (c) subjecting the low density fluid composition to depth filtration to yield a filtered low density fluid composition; (d) contacting the filtered low density fluid composition with at least one chromatography medium; and (e) collecting fluid containing the protein from the chromatography medium, thereby purifying the protein. In some embodiments of this aspect of the disclosure, the method further comprises subjecting the low density composition to any one or more of a second centrifugation step, a second filtration step, an acoustic wave separation step, a flocculation step or a precipitation step. In some embodiments, the low density composition and/or the high density composition is recycled through the decanter centrifuge, or through a bioreactor comprising a culture of the mammalian cells, which eventually is expected to result in another passage through the centrifuge. In some embodiments, the protein is an antibody or an antigen-binding fragment thereof, such as wherein the antibody or antigen-binding fragment thereof is a single-chain variable fragment, a Fv, a Fab, a Fab', a F(ab')2, a diabody, a triabody, a tetrabody, a BiTE, a Fd, a dAb, a minibody, or a maxibody. In some embodiments, the antibody or antigen-binding fragment thereof is a monoclonal antibody or antigen-binding fragment thereof. In some embodiments, the antibody or antigen-binding fragment thereof is contained in a chimera, such as a Chimeric Antigen Receptor.

The foregoing summary is not intended to define all aspects of the disclosure, and other features and advantages of the disclosure will become apparent from the following detailed description, including the drawings. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the invention narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

FIG. 1. Schematic illustration of a method of separating a protein produced in a mammalian cell from one or more mammalian cell components showing introduction of a fluid containing the protein into a decanter centrifuge and collection of a lower density fraction containing the protein and a higher density fraction containing cells, cell debris, aggregated protein, nucleic acids and other mammalian cell components. A) Separation involving a bioreactor for culturing mammalian cells, a decanter centrifuge for processing culture harvest in batch or continuous-flow mode, a harvest tank for collecting the low-density fraction containing the protein, and a waste tank for collecting the high-density fraction containing cells and cell components other than the protein. B) Separation in batch mode in which a surge tank is interposed between the bioreactor and the decanter centrifuge for collecting sufficient culture harvest to process, optionally including a flocculation step to induce aggregation, and separation, of light compounds. C) Separation scheme in which the higher-density fraction output from the decanter centrifuge is recirculated or recycled by returning it to the bioreactor. D) Separation scheme in which the lighter-density fraction output from the decanter centrifuge is recirculated or recycled by returning it to the bioreactor.

DETAILED DESCRIPTION

Figure 2:
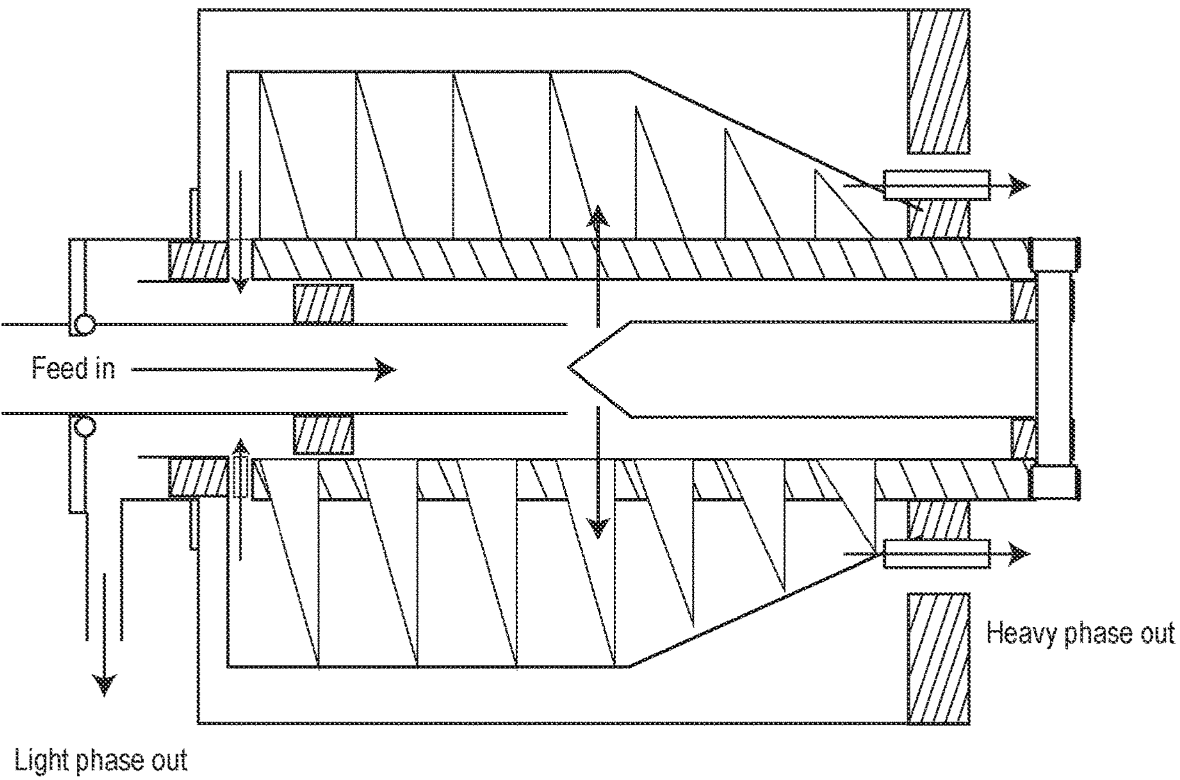
FIG. 2. Schematic illustration of a cross-section of a horizontally oriented decanter centrifuge. Culture fluid is introduced at the feed end of the centrifuge and the differential speed of the bowl and the scroll packs the denser material (e.g., cells) along the inner wall of the bowl, where the rotation of the scroll pushes the material toward the conical section of the bowl at the opposite end of the illustration. As the denser cells are compressed in the conical section of the bowl, the material is effectively "de-watered" and the resultant fluid flows over one or more weir plates to be channeled into a fluid discharge port at or near the outer shell of the decanter centrifuge.

The disclosure relates to the harvest recovery of large molecule proteins produced in mammalian cell culture through the use of decanter centrifuge technology. Harvest recovery operations for target biomolecules (e.g., biologics such as antibodies) that incorporate a separation step using a decanter centrifuge are suitable for continuous processing of cell culture fluid or for processing fed batch cell culture fluid. Typical modes of harvest for mammalian cell culture processes involves disk-stack centrifugation and/or depth filtration. Direct processing of cell culture fluid by filtration can operate continuously over a period of several days, but will exhibit fouling over time. The disk-stack centrifuge is a traditional method of mammalian cell culture harvest utilized when the entire bioreactor volume is harvested in a batch mode over the course of several hours. These traditional methods of harvesting biomolecules, such as proteins, from cell culture can lead to loss of up to 30% of the product. The introduction of decanter centrifuge technology to the process is innovative in that the state of the art held the view that decanter centrifugation could not discriminate between the densities of target proteins in cell culture fluid and biological particulates such as cells, cell debris, host cell proteins (HCPs) or nucleic acids (e.g., DNA) in that fluid. Disclosed herein is the surprising finding that decanter centrifugation can effect separation of target proteins, such as antibodies, from biological particulates typically found in cell culture fluid. Incorporating decanter centrifugation in the harvest recovery operation provides a means by which the protein may be harvested in a continuous stream over a long period of time, while still maintaining a clear flow path and minimizing fouling concerns for any subsequent filtration process steps, even with the higher cell densities of modern cell cultures (e.g., up to and beyond $10^8$ cells/ml). In addition, decanter centrifugation is well-suited for harvest recovery of target biomolecules such as antibodies from fed batch cultures, including high density fed batch cultures.

For continuously operated cell culture harvest processes, up to 30% of the culture productivity may currently be lost using the traditional harvesting means of depth filtration combined with cell density control for the bioreactor. Continuous decanter centrifuge operation has the potential to recover a significant additional portion of the harvest. Through the use of decanter centrifuge technology, also known as scroll decanter centrifuge technology, cell culture material may be separated into heavy (solids) and light (supernatant) streams. The methods of the disclosure described herein are applicable to several modes of harvesting product, specifically: (1) Continuous separation of protein from cellular material in a harvest stream of a continuous manufacturing process; (2) Continuous separation of protein from cellular material, followed by re-introduction of the cellular material to the bioreactor; and (3) Batch harvest of product from a bioreactor.

The scroll decanter centrifuge technology may be applied for the harvest from any type of bioreactor, including a stainless steel, glass, or plastic bioreactor. The scroll decanter centrifuge equipment itself may be constructed of stainless steel, glass, plastic, or another material, preferably stable in aqueous environments. In the case of a stainless steel construction, the equipment would be autoclaved and attached to the bioreactor via an aseptic connection. In some decanter centrifuges, the bowl is a composite of steel, e.g., stainless steel, and plastic.

Suitable harvest stream flow rates from cell culture bioreactors depend on several process design decisions. As a result, there is a wide range of harvest stream flow rates when compared across mammalian cell culture processes. In order to size the scroll decanter centrifuge equipment to fit the desired harvest flow rate, the operation of the unit may be either continuous, or operated in a periodic manner. When operated in a periodic, or batch, manner, one option is the addition of a surge tank that can be placed prior to the scroll decanter unit in order to collect product until a specific volume of cell culture fluid (containing the target biomolecule(s)) is met, at which point the equipment would be started and the material in the surge tank would be processed. The disclosure also contemplates batch, or periodic, harvest protocols that do not involve a surge tank.

Also noteworthy is that the disclosure provides methods of harvesting native or recombinant biomolecules (e.g., proteins) of interest produced in high-cell-density mammalian cell culture suspensions, e.g., CHO cell culture suspensions. The method makes use of continuous flow-through decanter centrifugation to harvest the biomolecules (e.g., proteins) of interest.

In greater detail, it can be understood that the harvest of target biomolecule has two parts: (1) the removal of cells, cell debris, and the like, and (2) clarification of the liquid. To achieve this result, many harvest methods have been employed. Centrifugation (e.g., disk-stack centrifugation) and filtration (e.g., depth filtration) are the current principal methods employed for mammalian cell culture harvest. Numerous filtration methods have been used, including membrane filtration, ultrafiltration, microfiltration, tangential flow filtration, alternative tangential flow filtration, and alluvial filtration. Other methods include acid precipitation, accelerated sedimentation such as flocculation, separation using gravity (e.g., by reducing or stopping culture agitation for a period of time), and acoustic wave separation. Exemplary precipitants are pH adjustments, and the use of insoluble salts such as calcium phosphate generated by adding a phosphate source to cell culture fluid containing calcium chloride. Commonly used flocculants include simple acids, divalent cations, polycationic polymers such as polyethyleneimine (PEI), non-ionic polymers such as polyalkylene glycols and transition metals, non-ionic surfactants, caprylic (octanoic) acid, and stimulus-responsive polymers such as benzylated poly(allylamine) used as flocculating compounds or attached to an insoluble matrix such as silica beads to aid settling. Often these methods are followed by depth filtration for further clarification. An exemplary depth filter is the 3M™ Zeta Plus™ Filter. Also contemplated are virus filters and/or sterilization filters, e.g., 3M™ LifeASSURE™ PDA Sterile Filter.

The disclosure provides a variety of cell culture processing methodologies involving a variety of harvest recovery steps that are related by separating the target biomolecule from at least some particulates in cell culture fluid in a decanter centrifuge. The disclosure contemplates methods in which one or more known techniques of cell culture processing are combined with separation via decanter centrifugation. For example, cell culture fluid to be subjected to decanter centrifuge separation can be initially processed by addition of any one or more of the flocculants or precipitants known in the art or disclosed herein. Moreover, in addition to decanter centrifuge separation, any of the known forms of filtration, such as depth filtration using cellulosic or synthetic fiber meshes. An exemplary depth filter is 3M™'s Zeta Plus™ Filter. Other suitable filtration technologies include virus filtration, sterilizing filtration such as filtration with the 3M™ LifeASSURE™ PDA Sterile Filter, membrane filtration, ultrafiltration, microfiltration, tangential flow filtration, alternative tangential flow filtration, and alluvial filtration. Further, methods according to the disclosure include harvest recovery operations including a separation via decanter centrifugation combined with separations via acoustic wave separation and/or simple gravity-driven settling. Beyond combining decanter centrifuge separation with any one or more known techniques useful in harvest recovery operations, the disclosure contemplates methods combining a harvest recovery operation containing a separation via decanter centrifugation with post-harvest recovery steps known in the art, such as target biomolecule recovery, e.g., affinity-based recovery which, for immunoglobulins and immunoglobulin-like targets may be based on binding of the target to Protein A, as well as chromatographic fractionations and polishing steps wherein the chromatographic medium can be in any form, including beads in column form, and the fractionations and polishing steps can rely on any discriminatory property of the target, such as size (e.g., size-exclusion chromatography), affinity, hydrophobicity (e.g., hydrophobic interaction chromatography), or any property known to be useful in discriminating among molecules using a chromatographic medium. Although not envisioned as a common embodiment of the disclosed methods, the disclosure further comprehends use of decanter centrifuge separation in combination with disk-stack centrifuge separation. In simple terms, the disclosure provides any methods for purifying a target biomolecule, e.g., biologic such as an antibody, that incorporates decanter centrifuge separation of the target from at least one particulate component of cell culture fluid.

The decanter centrifuge, or scroll decanter centrifuge, may be used to perform an initial separation into heavy (solids, including cells) and light (supernatant, including secreted recombinant protein) streams before reaching the rest of the harvest operation. Decanter centrifuges are commercially available from Lemitech, GmbH (Berlin, Germany), Alfa Laval (Richmond, VA), GEA Westfalia (Oelde, Germany); Centriquip (Manchester, England). Most decanter centrifuges on the market have stainless steel scrolls, or screws, but polyurethane scrolls with stainless steel cores are now available that provide improved performance relative to steel scrolls in being able to rotate faster due to lower weight, to last longer due to reduced friction between the scroll and the bowl, to lower cost, and to improve the work environment by lowering the noise associated with operation of the decanter centrifuge.

In operation, as shown in FIG. 1, cell culture removed from a bioreactor is delivered to the intake of a decanter centrifuge. A diagram showing a decanter centrifuge in horizontal orientation is shown in FIG. 2. The decanter centrifuge comprises a bowl having cylindrical and conical sections. Inside the bowl is at least one scroll, or screw. The decanter centrifuge is energized, resulting in the controlled rotation of the bowl and the scroll. In typical operation, the bowl and scroll are rotated at different speeds, typically through the use of variable frequency drives or different servo motors, allowing for individualized control of rotational speed, thereby resulting in a differential speed that facilitates separation of materials of different densities, e.g., solids and liquids. The use of different servo motors to control the rotation speeds of the bowl and scroll(s) allows for fine control of the differential speed. The centrifugal force associated with the rotation results in denser materials such as solids being pressed against the inside walls of the bowl. The differential speed determines the time that the denser materials (e.g., cells) are exposed to the centrifugal forces of the decanter centrifuge, which in turn determines the degree of separation of fluids and solids, in effect the degree of "de-watering" of the solid. The scroll(s) move the pressed solids from the walls of the bowl, through the cylindrical section of the bowl into the conical section of the bowl where these denser materials become further compacted. When the material being separated into components is a cell culture, the denser materials are cells, cell debris, and biomolecule aggregations. As the denser solid phase moves toward the conical end of the decanter centrifuge, it displaces fluid, which is then forced over at least one weir plate at the opposite end of the cylindrical section of the bowl, and into a fluid discharge stream. The geometry of the weir plate(s) in the centrifuge can affect the depth of clarification of the fluid. The bowl of the decanter centrifuge can be any composition known in the art, such as a metal, e.g., stainless steel, or plastic (e.g., polysulfone). There can be one or a plurality of scrolls of the same or differing compositions, and a typical scroll will be a screw of diameter and pitch known in the art to be effective in decanter centrifuges. The scroll(s) may be composed of any durable solid, such as a metal (e.g., stainless steel), plastic, or a combination of metal and plastic, such as a plastic decanter centrifuge with a metal bowl and scroll. The disclosure further contemplates scrolls of hybrid composition having a metal core (e.g., stainless steel) and plastic threads, e.g., polyurethane. Alternatively, the core and threads of a scroll may be composed of a metal such as stainless steel, with a plastic coating such as polyurethane applied to the outside edge of the threads. Analogously, bowls may be made of metal, such as stainless steel, glass, or plastic, or a hybrid composition of metal and plastic.

Methods according to the disclosure may involve any bioreactor known in the art for culture of biological solids (e.g., mammalian cells), including fermentation vessels, growth chambers, and chemostats made of any suitable material, such as a metal, e.g., stainless steel, or glass. Any decanter centrifuge known in the art can be used in such methods, with attention paid to associating a decanter centrifuge of a capacity appropriate to the desired volume and rate of cell culture removal from the bioreactor.

The disclosure provides for separation of recombinant proteins from cell culture fluid in a batch harvest stream from a cell culture bioreactor, where the cell culture fluid is passed through a decanter centrifuge, separating the solid materials, which are passed on to a waste receptacle, from the liquid supernatant which is collected in a harvest pool, FIG. 1A.

The disclosure provides for separation of recombinant proteins from cell culture fluid in a periodic harvest stream from a continuous cell culture process, where the cell culture fluid is passed through a surge tank/vessel prior to the decanter centrifuge separating the solid materials from the cell culture fluid which are passed on to a waste receptacle and the liquid supernatant is collected in a harvest pool, FIG. 1B.

The disclosure provides for separation of recombinant proteins from cell culture fluid in a continuous harvest stream from a continuous cell culture process, where the cell culture fluid is passed through a decanter centrifuge separating the solid materials from the cell culture fluid. In some embodiments, the solids may be recirculated or re-introduced into the bioreactor. The liquid supernatant is collected in a harvest pool (see FIG. 1C).

In some embodiments, flow rates through the decanter centrifuge can range from 16 mL/min to 133 mL/min. The harvest stream from the bioreactor depends on several process design decisions. As a result, there is a wide range around the harvest stream flow rates when compared across mammalian cell culture processes. For single batch harvests, higher flow rates are preferred. For the continuous harvest strategies, such as cell bleed product separation, lower flow rates are preferred. To size the decanter centrifuge to fit the desired harvest flow rate, the operation of the unit may be either continuous, or operated in a periodic manner. When operated in a periodic manner, a surge tank may be placed in the stream prior to the decanter centrifuge in order to collect product until a specific target volume is met, at which point the equipment would be started and the material in the surge tank would be processed for harvest. Batch or periodic harvest operations can also be undertaken without use of a surge tank.

As noted above and described in greater detail below, harvest operations involving decanter centrifuge separation can be combined with additional harvest strategies, including centrifugation, such as disk-stack centrifugation; filtration, including tangential flow filtration, microfiltration, ultrafiltration, and depth filtration; precipitation/sedimentation methods, such as flocculation; and chromatography media-based separations, typically using columns that include anion- and/or cation-exchange, affinity-based exchange (e.g., immunoaffinity exchange), molecular sieving, and/or polishing chromatography. Any purification or clarification protocol known in the art to be applicable to cell culture materials, including cell culture supernatant and fluids containing cellular materials, is comprehended by the methods disclosed herein. In a typical operation, separation via decanter centrifugation is the first step following removal of cell culture from a bioreactor (or a surge tank useful in batch-mode separations). The purification or clarification protocol may include any combination of downstream filters and/or columns and/or other forms of centrifugation useful in separating biomolecules such as proteins. The protocol may also include upstream precipitation or flocculation preceding decanter centrifuge separation.

Separation of a biomolecule (e.g., protein) of interest from other components in a bioreactor culture occurs early in processes designed to separate, or purify, that protein from a culture. The goals in separating the protein from other culture components is to maximize yield, minimize degradation, and minimize costs. Currently, many cell cultures, including mammalian cell cultures, are maintained at high density to achieve these goals. Initial harvest of a biomolecule (e.g., protein) of interest from such high density cultures at levels that exhibit satisfactory yield, activity and cost profiles has presented difficulties. The methods of the disclosure provide for an early, e.g., initial, separation step that sequesters a biomolecule (e.g., protein) of interest away from other cell culture components by employing a decanter centrifuge. That step alone significantly improves processes for harvesting biomolecules such as proteins, but the methods of the disclosure also extend to purification or separation processes that incorporate additional steps, such as centrifugation, filtration, precipitation/flocculation, and the like. The scope of the methods disclosed herein extend to any known purification or separation process for a biomolecule such as a protein if that purification or separation process is modified to incorporate a separation step using a decanter centrifuge.

Centrifugation beyond decanter centrifugation may also be used in purification processes according to the disclosure. The development of disk-stack centrifugation has provided a technique for separating substances on the basis of density differences that involves relatively low, or absent, shear forces, that is suitable for incorporation into harvest processes involving mammalian cells and biomolecules. The technique does have limitations, such as variation in clarification upon scale-up due to a variety of factors that are not fully understood. Moreover, while shear forces are relatively low, they are not absent and this contributes to undesired cell lysis and degradation. Furthermore, negatively charged compounds at harvest pH can form colloids that clog the disks of the centrifuge. Additional factors, such as cell culture properties, centrifuge feed rate, bowl geometry, and rotation speed combine to place limits on the particle densities that can be effectively separated by disk centrifugation. Notwithstanding these limitations, and even though disk-stack centrifugation may be seen as largely redundant over decanter centrifuge separations, the disclosure contemplates target biomolecule purification methods incorporating separations by both decanter centrifugation and disk-stack centrifugation.

Filtration is another known technique generally useful in separation processes that can be combined with decanter centrifuge separation. Often, depth filtration is coupled to centrifugation steps, including disk centrifugation, to address the particle densities that could not be separated by centrifugation, thereby further clarifying the separated materials of interest, such as proteins solutions being separated from cultured cells, cell debris, media components, and the like. Suitable depth filters are composed of porous matrices of cellulosic fibers, optionally attached to charged resins used to attract and retain oppositely charged filter aids, as would be known in the art. Some exemplary depth filters incorporate diatomaceous earth as an inorganic filter aid. Depth filters may also contain binders. For cellulosic depth filters, as for all depth filters, the thicker the material, i.e., the cellulosic fiber mat or material, the more sinuous and complicated is the path through the filter material, which results in particles of various sizes being captured and removed from the fluid being clarified. Cellulosic depth filters typically have a net positive charge, which also provides a basis for adsorptive removal of some components/particles. Unfortunately, cellulose-based fibers tend to have both organic and inorganic contaminants that are extracted by the fluid to be clarified, resulting in the time and expense required to prepare the filters by pre-rinsing or accepting the lowered purity and yield attributable, at least in part, to the contaminants released from the filter.

A significant issue with all filtration methodologies is clogging of the pores of the filter. For culture-based separations, this is a major problem that has limited the use of filtering technologies. In general, the trouble filtration technologies have in handling high-density cell culture fluids results in in the need to remove, or "bleed", cells to yield lower-density cell culture fluids, resulting in losses reducing the efficiencies associated with filtration technologies. Tangential flow filtration, including tangential flow microfiltration, was designed to minimize the clogging of filter pores by flowing the material to be subjected to the harvest process across the filter surface, i.e., in a direction approximately 90° displaced from the effective direction of the material of interest successfully being purified, such as a biomolecule (e.g., protein) of interest (e.g., a monoclonal antibody). Stated in simple terms, if the filter is viewed as an approximately two-dimensional plane, the material to be separated would flow across a face of the membrane while the component of interest would enter pores of the filter and traverse the small thickness of the generally planar filter, a direction perpendicular to the flow of the material to be separated. Apparent in all tangential flow filtration technologies is the need for recirculation to obtain acceptable yields because in flowing cell culture fluid tangential to the filter, the bulk of the material to be separated, including the component of interest, will move tangentially past the filter. Thus, the design has inherent inefficiencies, but is effective in minimizing clogging while providing a gentle means of achieving a degree of separation.

Beyond centrifugation and/or filtration, the methods of the disclosure may further incorporate precipitation and/or flocculation. Although more typically found in chemical separation processes, these techniques can be useful in processes for separating biomolecules, often as adjuncts to centrifugation and/or filtration. Exemplary precipitants are pH adjustments, and insoluble salts such as calcium phosphate generated in situ. There are a wide variety of flocculants suitable for use in separating biomolecules, including simple acids, divalent cations, polycationic polymers such as PEI, non-ionic polymers such as polyalkylene glycols and transition metals, non-ionic surfactants, caprylic acid, and stimulus-responsive smart polymers such as benzylated poly (allylamine). Flocculants can be added at any of several stages in the harvest process. Typically, flocculants would be added prior to liquid stream introduction into the scroll decanter (FIGS. 1A, 1B). Alternatively or in conjunction, flocculants are added to the harvested liquid stream prior to further downstream processing (FIG. 1B). Alternatively, flocculant is added in either place indicated in FIG. 1C or 1D to avoid having flocculant in the recycle stream. Despite advances in precipitation and flocculation technologies, these techniques still pose the difficulty of later removing the agents, particularly if the agent can have a toxic effect on anyone subsequently receiving the purified target biomolecule. Failure to effectively remove the agents reduces the clarification by both their presence and their capacity to induce downstream flocculation or precipitation.

The methods disclosed herein also include incorporation of acoustic wave separation before or after a decanter centrifugation step. Acoustic wave separation establishes a standing acoustic wave that traps cells in culture flowing through a flow channel in which the standing wave is located. The cells are captured in nodes of the standing wave, leading to cell aggregations that progressively diminish the buoyancy of the cells, allowing for their separation. The technique can be accomplished in a device of modest dimensions and acoustic wave separation minimizes damage to cells and cell substituents such as proteins while avoiding deleterious temperature changes. Methods according to the disclosure contemplate incorporation of acoustic wave separation in conjunction with, or as a substitute for, centrifugation techniques such as disk centrifugation separation.

Beyond the foregoing technologies, the methods of the disclosure contemplate a wide variety of chromatographic steps involved in separating, or clarifying, biomolecules (e.g., proteins) of interest, including size exclusion chromatography, ion exchange chromatography, and affinity chromatography, such as immunoaffinity chromatography. Various media may be used in a variety of configurations designed to contribute to biomolecule, e.g., protein, separations in batch and continuous modes of purification.

The methods disclosed herein also embrace incorporation of recent advances in separation technology in the culture extraction and purification/clarification protocols. For example a decanter centrifuge is used in combination with a hybrid purification device such as a device that combines ion exchange (e.g., anion exchange) chromatography with molecular sieve or size exclusion chromatography, as is found in the 3M™ Emphaze™ AEX Hybrid Purifier, optionally incorporating any of the molecule separation technologies noted, or alluded to, above. The scale of operation of the methods according to the disclosure is adaptable, with the capacity to handle small batch or continuous mode separations, pilot-scale separations, or fully commercialized separations.

As noted above, where multiple harvest strategies are used, the decanter centrifuge is positioned between the bioreactor and the second harvest method, receiving bulk or continuous streams, or bleeds, of cell culture media from the bioreactor or surge vessel and passing on clarified fluid to the rest of the harvest operation.

Biomolecule (e.g., Protein) of Interest

The terms "polypeptide" or "protein" are used interchangeably throughout and refer to a molecule comprising two or more amino acid residues joined to each other by peptide bonds. Polypeptides and proteins also include macromolecules having one or more deletions from, insertions to, and/or substitutions of the amino acid residues of the native sequence, that is, a polypeptide or protein produced by a naturally occurring and non-recombinant cell; or is produced by a genetically engineered or recombinant cell, and comprise molecules having one or more deletions from, insertions to, and/or substitutions of the amino acid residues of the amino acid sequence of the native protein. Polypeptides and proteins also include amino acid polymers in which one or more amino acids are chemical analogs of a corresponding naturally-occurring amino acid and polymers. Polypeptides and proteins are also inclusive of modifications including, but not limited to, glycosylation, lipid attachment, sulfation, gamma-carboxylation of glutamic acid residues, hydroxylation and ADP-ribosylation.

The terms "polynucleotide", "nucleic acid molecule", or "engineered nucleic acid molecule" are used interchangeably throughout and include both single-stranded and double-stranded nucleic acids and includes genomic DNA, RNA, mRNA, cDNA, or synthetic origin or some combination thereof which is not associated with sequences normally found in nature. The terms "isolated polynucleotide", "isolated nucleic acid molecule" or "isolated engineered nucleic acid molecule" specifically refer to sequences of synthetic origin or those not normally found in nature. Isolated nucleic acid molecules comprising specified sequences may include, in addition to the specified sequences, coding sequences for up to ten or even up to twenty other proteins or portions thereof or may include operably linked regulatory sequences that control expression of the coding region of the recited nucleic acid sequences, and/or may include vector sequences. The nucleotides comprising the nucleic acid molecules can be ribonucleotides or deoxyribonucleotides or a modified form of either type of nucleotide. The modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

Biomolecules (e.g., polypeptides and proteins) of interest can be of scientific or commercial interest, including protein-based therapeutics. Biomolecules (e.g., proteins) of interest include, among other things, secreted proteins, non-secreted proteins, intracellular proteins or membrane-bound proteins. Biomolecules of interest can be produced by recombinant animal cell lines using cell culture methods and may be referred to as "recombinant proteins". The expressed protein(s) may be produced intracellularly or secreted into the culture medium from which it can be recovered and/or collected. The term "isolated protein" or "isolated recombinant protein" refers to a polypeptide or protein of interest, that is purified away from proteins or polypeptides or other contaminants that would interfere with its therapeutic, diagnostic, prophylactic, research or other use. Biomolecules of interest include proteins that exert a therapeutic effect by binding a target, particularly a target among those listed below, including targets derived therefrom, targets related thereto, and modifications thereof.

By "purifying" is meant increasing the degree of purity of the protein in the composition by removing (partially or completely) at least one product-related impurity from the composition. Recovery and purification of proteins is accomplished by any downstream process, particularly the harvest operation, resulting in a more "homogeneous" protein composition that meets yield and product quality targets (such as reduced product-related impurities and increased product quality).

As used herein, the term "isolated" means (i) free of at least some other proteins or polynucleotides with which it would normally be found, (ii) is essentially free of other proteins or polynucleotides from the same source, e.g., from the same species, (iii) separated from at least about 50 percent of polypeptides, polynucleotides, lipids, carbohydrates, or other materials with which it is associated in nature, (iv) operably associated (by covalent or noncovalent interaction) with a polypeptide or polynucleotide with which it is not associated in nature, or (v) does not occur in nature.

Biomolecules (e.g., proteins) of interest include "antigen-binding proteins". Antigen-binding protein refers to proteins or polypeptides that comprise an antigen-binding region or antigen-binding portion that has affinity for another molecule to which it binds (antigen). Antigen-binding proteins encompass antibodies, peptibodies, antibody fragments, antibody derivatives, antibody analogs, fusion proteins (including single-chain variable fragments (scFvs) and double-chain (divalent) scFvs), muteins, multispecific proteins, and bispecific proteins.

An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen.

The term "antibody" includes reference to both glycosylated and non-glycosylated immunoglobulins of any isotype or subclass or to an antigen-binding region thereof that competes with the intact antibody for specific binding. Unless otherwise specified, antibodies include human, humanized, chimeric, multi-specific, monoclonal, polyclonal, heteroIgG, bispecific, and oligomers or antigen binding fragments thereof. Antibodies include the IgG1-, IgG2-, IgG3- or IgG4-type. Also included are proteins having an antigen binding fragment or region such as Fab, Fab', F(ab')2, Fv, diabodies, Fd, dAb, maxibodies, single chain antibody molecules, single domain $V_HH$, complementarity determining region (CDR) fragments, scFv, diabodies, triabodies, tetrabodies and polypeptides that contain at least a portion of an immunoglobulin that is sufficient to confer specific antigen binding to a target polypeptide.

Also included are human, humanized, and other antigen-binding proteins, such as human and humanized antibodies, that do not engender significantly deleterious immune responses when administered to a human.

Modified proteins are also included, such as are proteins modified chemically by a non-covalent bond, covalent bond, or both a covalent and non-covalent bond. Also included are proteins further comprising one or more post-translational modifications which may be made by cellular modification systems or modifications introduced ex vivo by enzymatic and/or chemical methods or introduced in other ways.

Multispecific constructs, "multispecific protein", and "multispecific antibody" are used herein to refer to proteins that are recombinantly engineered to simultaneously bind and neutralize at least two different antigens or at least two different epitopes on the same antigen. For example, multispecific proteins may be engineered to target immune effectors in combination with targeting cytotoxic agents to tumors or infectious agents. Multispecific proteins include trispecific antibodies, tetravalent bispecific antibodies, multispecific proteins without antibody components such as dia-, tria- or tetrabodies, minibodies, and single chain proteins capable of binding multiple targets. Coloma, M. J., et al., Nature Biotech. 15 (1997) 159-163.

The most common and most diverse group of multispecific proteins are those that bind two antigens, referred to herein as "bispecific", "bispecific constructs", "bispecific proteins", and "bispecific antibodies". Bispecific proteins can be grouped in two broad categories: immunoglobulin G (IgG)-like molecules and non-IgG-like molecules. IgG-like molecules retain Fc-mediated effector functions, such as antibody-dependent cell mediated cytotoxicity (ADCC), complement-dependent cytotoxicity (CDC), and antibody-dependent cellular phagocytosis (ADCP), the Fc region helps improve solubility and stability and facilitate some purification operations. Non-IgG-like molecules are smaller, enhancing tissue penetration (see Sedykh et al., Drug Design, Development and Therapy 18(12), 195-208, 2018; Fan et al., J Hematol & Oncology 8:130-143, 2015; Spiess et al., Mol Immunol 67, 95-106, 2015; Williams et al., Chapter 41 Process Design for Bispecific Antibodies in Biopharmaceutical Processing Development, Design and Implementation of Manufacturing Processes, Jagschies et al., eds., 2018, pages 837-855. Bispecific proteins are sometimes used as a framework for additional components having binding specificities to different antigens or numbers of epitopes, increasing the binding specificity of the molecule.

The formats for bispecific proteins, which include bispecific antibodies, are constantly evolving and include, but are not limited to, single chain antibodies, quadromas, knobs-in-holes, cross-Mabs, dual variable domains IgG (DVD-IgG), IgG-single chain Fv (scFv), scFv-CH3 KIH, dual action Fab (DAF), half-molecule exchange, κλ-bodies, tandem scFv, scFv-Fc, diabodies, single chain diabodies (sc-Diabodies), scDiabodies-CH3, triple body, miniantibody, minibody, TriBi minibody, tandem diabodies, scDiabody-HAS, Tandem scFv-toxin, dual-affinity retargeting molecules (DARTs), nanobody, nanobody-HSA, dock and lock (DNL), strand exchange engineered domain SEEDbody, Triomab, leucine zipper (LUZ-Y), XmAb®; Fab-arm exchange, DutaMab, DT-IgG, charged pair, Fcab, orthogonal Fab, IgG(H)-scFv, scFV-(H)IgG, IgG(L)-scFV, IgG (L1H1)-Fv, IgG(H)-V, V(H)-IgG, IgG(L)-V V(L)-IgG, KIH IgG-scFab, 2scFV-IgG, IgG-2scFv, scFv4-Ig, Zybody, DVI-Ig4 (four-in-one), Fab-scFv, scFv-CH-CL-scFV, F(ab')2-scFv2, scFv-KIH, Fab-scFv-Fc, tetravalent HCAb, scDiabody-Fc, diabody-Fc, intrabody, ImmTAC, HSABody, IgG-IgG, Cov-X-Body, scFv1-PEG-scFv2, bi-specific T cell engagers (BiTE®s) and half-life extended bispecific T cell engagers (HLE BiTE®s), heterolg BiTE®s (Fan supra; Spiess supra; Sedykh supra; Seimetz et al., Cancer Treat Rev 36(6) 458-67, 2010; Shulka and Norman, Chapter 26 Downstream Processing of Fc Fusion Proteins, Bispecific Antibodies, and Antibody-Drug Conjugates, in Process Scale Purification of Antibodies Second Edition, Uwe Gottschalk editor, p559-594, John Wiley & Sons, 2017; Moore et al., MAbs 3:6, 546-557, 2011). Biomolecules (e.g., proteins) of interest may also include recombinant fusion proteins comprising, for example, a multimerization domain, such as a leucine zipper, a coiled coil, an Fc portion of an immunoglobulin, and the like. Also included are proteins comprising all or part of the amino acid sequences of differentiation antigens (referred to as CD proteins) or their ligands or proteins substantially similar to either of these.

Biomolecules (e.g., proteins) of interest also include genetically engineered receptors such as chimeric antigen receptors (CARs or CAR-Ts) and T cell receptors (TCRs), as well as other proteins comprising an antigen binding molecule that interacts with that targeted antigen. CARs can be engineered to bind to an antigen (such as a cell-surface antigen) by incorporating an antigen binding molecule that interacts with that targeted antigen. CARs typically incorporate an antigen binding domain (such as scFv) in tandem with one or more costimulatory ("signaling") domains and one or more activating domains.

In some embodiments, biomolecules (e.g., proteins) of interest may include colony stimulating factors, such as granulocyte colony-stimulating factor (G-CSF). Such G-CSF agents include, but are not limited to, Neupogen® (filgrastim) and Neulasta® (pegfilgrastim). Also included are erythropoiesis stimulating agents (ESA), such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, epoetin omega, epoetin iota, tissue plasminogen activator, GLP-1 receptor agonists, as well as the molecules or variants or analogs thereof and biosimilars of any of the foregoing.

In some embodiments, biomolecules (e.g., proteins) of interest may include proteins that bind specifically to one or more CD proteins, HER receptor family proteins, cell adhesion molecules, growth factors, nerve growth factors, fibroblast growth factors, transforming growth factors (TGF), insulin-like growth factors, osteoinductive factors, insulin and insulin-related proteins, coagulation and coagulation-related proteins, colony stimulating factors (CSFs), other blood and serum proteins blood group antigens; receptors, receptor-associated proteins, growth hormones, growth hormone receptors, T-cell receptors; neurotrophic factors, neurotrophins, relaxins, interferons, interleukins, viral antigens, lipoproteins, integrins, rheumatoid factors, immunotoxins, surface membrane proteins, transport proteins, homing receptors, addressins, regulatory proteins, and immunoadhesins.

In some embodiments, biomolecules (e.g., proteins) of interest bind to one of more of the following, alone or in any combination: CD proteins including but not limited to CD3, CD4, CD5, CD7, CD8, CD19, CD20, CD22, CD25, CD30, CD33, CD34, CD38, CD40, CD70, CD123, CD133, CD138, CD171, and CD174, HER receptor family proteins, including, for instance, HER2, HER3, HER4, and the EGF receptor, EGFRvIII, cell adhesion molecules, for example, LFA-1, Mol, p150,95, VLA-4, ICAM-1, VCAM, and alpha v/beta 3 integrin, growth factors, including but not limited to, for example, vascular endothelial growth factor ("VEGF"); VEGFR2, growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), Cripto, transforming growth factors (TGF), including, among others, TGF-α and TGF-β, including TGF-β1, TGF-β2, TGF-β3, TGF-β4, or TGF-β5, insulin-like growth factors-I and -II (IGF-I and IGF-II), des(1-3)-IGF-I (brain IGF-I), and osteoinductive factors, insulins and insulin-related proteins, including but not limited to insulin, insulin A-chain, insulin B-chain, proinsulin, and insulin-like growth factor binding proteins; (coagulation and coagulation-related proteins, such as, among others, factor VIII, tissue factor, von Willebrand factor, protein C, alpha-1-antitrypsin, plasminogen activators, such as urokinase and tissue plasminogen activator ("t-PA"), bombazine, thrombin, thrombopoietin, and thrombopoietin receptor, colony stimulating factors (CSFs), including the following, among others, M-CSF, GM-CSF, and G-CSF, other blood and serum proteins, including but not limited to albumin, IgE, and blood group antigens, receptors and receptor-associated proteins, including, for example, flk2/flt3 receptor, obesity (OB) receptor, growth hormone receptors, and T-cell receptors; neurotrophic factors, including but not limited to, bone-derived neurotrophic factor (BDNF) and neurotrophin-3, -4, -5, or -6 (NT-3, NT-4, NT-5, or NT-6); relaxin A-chain, relaxin B-chain, and prorelaxin, interferons, including for example, interferon-alpha, -beta, and -gamma, interleukins (ILs), e.g., IL-1 to IL-10, IL-12, IL-15, IL-17, IL-23, IL-12/IL-23, IL-2Ra, IL1-R1, IL-6 receptor, IL-4 receptor and/or IL-13 to the receptor, IL-13RA2, or IL-17 receptor, IL-1RAP, IL1-α, IL-1β, viral antigens, including but not limited to, an AIDS envelope viral antigen, lipoproteins, calcitonin, glucagon, atrial natriuretic factor, lung surfactant, tumor necrosis factor-alpha and -beta, enkephalinase, BCMA, IgKappa, ROR-1, ERBB2, mesothelin, RANTES (regulated on activation normally T-cell expressed and secreted), mouse gonadotropin-associated peptide, Dnase, FR-alpha, inhibin, and activin, integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, MIC (MIC-a, MIC-B), ULBP 1-6, EPCAM, PSA, addressins, regulatory proteins, immunoadhesins, antigen-binding proteins, somatropin, CTGF, CTLA4, eotaxin-1, MUC1, CEA, c-MET, Claudin-18, GPC-3, EPHA2, FPA, LMP1, MG7, NY-ESO-1, PSCA, ganglioside GD2, ganglioside GM2, BAFF, OPGL (RANKL), myostatin, Dickkopf-1 (DKK-1), Ang2, NGF, IGF-1 receptor, hepatocyte growth factor (HGF), TRAIL-R2, c-Kit, B7RP-1, PSMA, P-cadherin, NKG2D-1, programmed cell death protein 1 and ligand, PD1 and PDL1, mannose receptor/hCGβ, hepatitis-C virus, mesothelin dsFv [PE38 conjugate, *Legionella pneumophila* (IIy), gpA33, B7H3, IFN gamma, interferon gamma induced protein 10 (IP10), IFNAR, TALL-1, thymic stromal lymphopoietin (TSLP), proprotein convertase subtilisin/Kexin Type 9 (PCSK9), stem cell factors, Flt-3, calcitonin gene-related peptide (CGRP), OX40L, α4β7, platelet specific (platelet glycoprotein Iib/IIIb (PAC-1), transforming growth factor beta (TFGβ), Zona pellucida sperm-binding protein 3 (ZP-3), TWEAK, platelet derived growth factor receptor alpha (PDGFRα), sclerostin, and biologically active fragments or variants of any of the foregoing.

In some embodiments, biomolecules (e.g., proteins) of interest include abciximab, adalimumab, adecatumumab, aflibercept, alemtuzumab, alirocumab, anakinra, atacicept, basiliximab, belimumab, bevacizumab, biosozumab, brentuximab vedotin, brodalumab, cantuzumab mertansine, canakinumab, cetuximab, certolizumab pegol, conatumumab, daclizumab, denosumab, eculizumab, edrecolomab, efalizumab, epratuzumab, etanercept, evolocumab, galiximab, ganitumab, gemtuzumab, golimumab, ibritumomab tiuxetan, infliximab, ipilimumab, lerdelimumab, lumiliximab, lxdkizumab, mapatumumab, motesanib diphosphate, muromonab-CD3, natalizumab, nesiritide, nimotuzumab, nivolumab, ocrelizumab, ofatumumab, omalizumab, oprelvekin, palivizumab, panitumumab, pembrolizumab, pertuzumab, pexelizumab, ranibizumab, rilotumumab, rituximab, romiplostim, romosozumab, sargamostim, tocilizumab, tositumomab, trastuzumab, ustekinumab, vedolizumab, visilizumab, volociximab, zanolimumab, zalutumumab, and biosimilars of any of the foregoing.

In some embodiments, biomolecules (e.g., proteins) of interest may include blinatumomab, catumaxomab, ertumaxomab, solitomab, targomiRs, lutikizumab (ABT981), vanucizumab (RG7221), remtolumab (ABT122), ozoralixumab (ATN103), floteuzmab (MGD006), pasotuxizumab (AMG112, MT112), lymphomun (FBTA05), (ATN-103), AMG211 (MT111, Medi-1565), AMG330, AMG420 (B1836909), AMG-110 (MT110), MDX-447, TF2, rM28, HER2Bi-aATC, GD2Bi-aATC, MGD006, MGD007, MGD009, MGD010, MGD011 (JNJ64052781), IMCgp100, indium-labeled IMP-205, xm734, LY3164530, OMP-305BB3, REGN1979, COV322, ABT112, ABT165, RG-6013 (ACE910), RG7597 (MEDH7945A), RG7802, RG7813(RO6895882), RG7386, BITS7201A (RG7990), RG7716, BFKF8488A (RG7992), MCLA-128, MM-111, MM141, MOR209/ES414, MSB0010841, ALX-0061, ALX0761, ALX0141; BII034020, AFM13, AFM11, SAR156597, FBTA05, PF06671008, GSK2434735, MEDI3902, MEDI0700, MEDI7352, as well as the molecules or variants or analogs thereof and biosimilars of any of the foregoing.

Biomolecules (e.g., proteins) of interest according to the disclosure encompass all of the foregoing and further include antibodies comprising 1, 2, 3, 4, 5, or 6 of the complementarity determining regions (CDRs) of any of the aforementioned antibodies. Also included are variants that comprise a region that is 70% or more, especially 80% or more, more especially 90% or more, yet more especially 95% or more, particularly 97% or more, more particularly 98% or more, yet more particularly 99% or more identical in amino acid sequence to a reference amino acid sequence of a biomolecule of interest in the form of a protein. Identity in this regard can be determined using a variety of well-known and readily available amino acid sequence analysis software. Preferred software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by MasPar.

Chimeric antigen receptors incorporate one or more costimulatory (signaling) domains to increase their potency. See U.S. Pat. Nos. 7,741,465, and 6,319,494, as well as Krause et al and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). Suitable costimulatory domains can be derived from, among other sources, CD28, CD28T, OX40, 4-1BB/CD137, CD2, CD3 (alpha, beta, delta, epsilon, gamma, zeta), CD4, CD5, CD7, CD8, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CDI Ia/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CDI-Id, ITGAE, CD103, ITGAL, CDI-Ia, LFA-1, ITGAM, CDI-Ib, ITGAX, CDI-Ic, ITGBI, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, 41-BB, GADS, SLP-76, PAG/Cbp, CD19a, CD83 ligand, or fragments or combinations thereof. The costimulatory domain can comprise one or more of an extracellular portion, a transmembrane portion, and an intracellular portion.

Expression Systems

Expression systems and constructs in the form of plasmids, expression vectors, transcription or expression cassettes that comprise one or more polynucleotides encoding a biomolecule (e.g., protein) of interest as provided herein, as well host cells comprising such expression systems or constructs. As used herein, "vector" means any molecule or entity (e.g., nucleic acid, plasmid, bacteriophage, transposon, cosmid, chromosome, virus, virus capsid, virion, naked DNA, complexed DNA and the like) suitable for use to transfer and/or transport protein encoding information into a host cell and/or to a specific location and/or compartment within a host cell. Vectors can include viral and non-viral vectors, non-episomal mammalian vectors. Vectors are often referred to as expression vectors, for example, recombinant expression vectors and cloning vectors. The vector may be introduced into a host cell to allow replication of the vector itself and thereby amplify the copies of the polynucleotide contained therein. The cloning vectors may contain sequence components that generally include, without limitation, an origin of replication, promoter sequences, transcription initiation sequences, enhancer sequences, transposons/transposases, and selectable markers. These elements may be selected as appropriate by a person of ordinary skill in the art.

Host Cells

"Cell" or "Cells" include any prokaryotic or eukaryotic cell. Cells can be either ex vivo, in vitro or in vivo, either separate or as part of a higher structure such as a tissue or organ. Cells include "host cells", also referred to as "cell lines", which are genetically engineered to express a protein of commercial or scientific interest. Host cells are typically derived from a lineage arising from a primary culture that can be maintained in culture for an unlimited time. Genetically engineering the host cell involves transfecting, transforming or transducing the cells with a recombinant polynucleotide molecule, and/or otherwise altering (e.g., by homologous recombination and gene activation or fusion of a recombinant cell with a non-recombinant cell) to cause the host cell to express a desired protein. Methods and vectors for genetically engineering cells and/or cell lines to express biomolecules (e.g., proteins) of interest are well known to those of skill in the art.

A host cell can be any prokaryotic cell (for example, *E. coli*) or eukaryotic cell (for example, yeast, insect, or animal cells (e.g., CHO cells)). Vector DNA can be introduced into prokaryotic or eukaryotic cells via conventional transformation or transfection techniques.

Host cells, when cultured under appropriate conditions, express the protein of interest that can be subsequently collected from the culture medium (if the host cell secretes it into the medium) or directly from the host cell producing it (if it is not secreted). The selection of an appropriate host cell will depend upon various factors, such as desired expression levels, protein modifications that are desirable or necessary for activity (such as glycosylation or phosphorylation) and ease of folding into a biologically active molecule.

By "culture" or "culturing" is meant the growth and propagation of cells outside of a multicellular organism or tissue. Suitable culture conditions for mammalian cells are known in the art. Cell culture media and tissue culture media are interchangeably used to refer to media suitable for growth of a host cell during in vitro cell culture. Typically, cell culture media contains a buffer, salts, energy source, amino acids, vitamins and trace essential elements. Any media capable of supporting growth of the appropriate host cell in culture can be used. Cell culture media, which may be further supplemented with other components to maximize cell growth, cell viability, and/or recombinant protein production in a particular cultured host cell, are commercially available and include RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series, among others, which can be obtained from the American Type Culture Collection or SAFC Biosciences, as well as other vendors. Cell culture media can be serum-free, protein-free, growth factor-free, and/or peptone-free media. Cell culture may also be enriched by the addition of nutrients and used at greater than its usual, recommended concentrations.

Various media formulations can be used during the life of the culture, for example, to facilitate the transition from one stage (e.g., the growth stage or phase) to another (e.g., the production stage or phase) and/or to optimize conditions during cell culture (e.g., concentrated media provided during perfusion culture). A growth medium formulation can be used to promote cell growth and minimize protein expression. A production medium formulation can be used to promote production of the biomolecule (e.g., protein) of interest and maintenance of the cells, with a minimal of new cell growth). A feed media, typically a media containing more concentrated components such as nutrients and amino acids, which are consumed during the course of the production phase of the cell culture may be used to supplement and maintain an active culture, particularly a culture operated in fed batch, semi-perfusion, or perfusion mode. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift.

Host cells may be cultured in suspension or in an adherent form, attached to a solid substrate. Cell cultures can be established in fluidized bed bioreactors, hollow fiber bioreactors, roller bottles, shake flasks, or stirred tank bioreactors, with or without microcarriers.

Cell cultures can be operated in a batch, fed batch, continuous, semi-continuous, or perfusion mode. Mammalian cells, such as CHO cells, may be cultured in bioreactors at a smaller scale of less than 100 ml to less than 1000 ml. Alternatively, larger scale bioreactors that contain 1000 ml to over 20,000 liters of media can be used. Large scale cell cultures, such as for clinical and/or commercial scale biomanufacturing of protein therapeutics, may be maintained for weeks and even months, while the cells produce the desired protein(s).

Harvest

The harvested recombinant biomolecule of interest in the form of a protein can then be purified, or partially purified, away from any impurities, such as remaining cell culture media, cell extracts, undesired components, host cell proteins, improperly expressed proteins, product-related impurities, and the like, through one or more downstream unit operations using the methods described herein Downstream Purification Purification of a biomolecule such as an antibody biologic from the cell culture fluid typically begins with decanter centrifuge separation in the methods according to the disclosure. Following harvest recovery operations, the purification process continues with capture chromatography. Capture chromatography makes use of media, such as resins, membranes, gels and the like, that will bind to the target biomolecule of interest, for example using affinity chromatography, size exclusion chromatography, ion exchange chromatography, hydrophobic interaction chromatography (HIC), immobilized metal affinity chromatography (IMAC), and the like. Such materials are known in the art and are commercially available. Affinity chromatography options may comprise a substrate-binding capture mechanism, an aptamer-binding capture mechanism, or a cofactor-binding capture mechanism, for example. For proteins containing an Fc component, an antibody- or antibody fragment-binding capture mechanism such as Protein A, Protein G, Protein A/G, and Protein L can be used. The recombinant protein of interest can be tagged with a polyhistidine tag or an epitope, such a FLAG® and subsequently purified by using a specific antibody directed to such epitope.

To ensure patient safety, viral inactivation and virus filtration have become a typical component of the purification process when manufacturing protein therapeutics. Various methods can be employed for virus inactivation and include heat inactivation/pasteurization, UV and gamma ray irradiation, use of high intensity broad spectrum white light, addition of chemical inactivating agents, surfactants, and solvent/detergent treatments. During the downstream process virus inactivation and/or virus filtration can be performed one or more times to remove viral matter from the composition comprising the biomolecule (e.g., protein) of interest. One method for achieving virus inactivation is incubation at low pH or other suitable solution conditions for achieving the inactivation of viruses. Low pH virus inactivation can be followed with a neutralization operation that readjusts the viral inactivated solution to a pH more compatible with the requirements of the following unit operations. Viral inactivated or neutralized viral inactivated eluate pools may also be followed by filtration, such as depth filtration, to remove any resulting turbidity or precipitation. Viral filtration can be performed using micro- or nano-filters, such as those available from Asahi Kasei (Plavona®) and EDM Millipore (VPro®).

The term "polishing" is used herein to refer to one or more chromatographic steps performed to remove remaining contaminants and impurities such as DNA, host cell proteins, product-specific impurities, variant products and aggregates, and virus adsorption from a fluid composition comprising a target biomolecule that is close to a final desired purity. Polish chromatography makes use of media, such as resins and/or membranes, containing agents that can be used in either a flow-through mode (where the protein flows through the resin/membrane and is contained in the flow-through eluent while the contaminants and impurities are bound to the chromatography medium) or bind and elute mode (where the biomolecule of interest is bound to the chromatography medium and is eluted after the contaminants and impurities have flowed through or been washed off the chromatography medium). Examples of such polish chromatography operations include ion exchange chromatography (IEX), including anion exchange chromatography (AEX) and/or cation exchange chromatography (CEX); hydrophobic interaction chromatography (HIC); mixed modal or multimodal chromatography (MM), hydroxyapatite chromatography (HA); reverse-phase chromatography, size exclusion chromatography (SEC), and gel filtration.

Product concentration and buffer exchange of the biomolecule of interest into a desired formulation buffer for bulk storage of the drug substance are typically accomplished by ultrafiltration and diafiltration unit operation prior to the final fill and finish of the drug product.

All patents and other publications identified are expressly incorporated herein by reference in their entirety or in relevant part, as would be apparent from the context of the citation, for the purpose of describing and disclosing, for example, the methodologies described in such publications that might be used in connection with information described herein.

What is claimed is:

1. A method for separating protein produced in a mammalian cell from at least one other mammalian cell component comprising:

(a) introducing a continuous stream of a fluid comprising mammalian cells from a bioreactor into at least one decanter centrifuge;

(b) operating the decanter centrifuge, thereby separating fluid components into a low density composition and a high density composition;

(c) recycling the low density composition through the bioreactor;

(d) collecting the low density composition or recycling the low density composition through the decanter centrifuge; and (e) recycling the high density composition through the decanter centrifuge, wherein the fluid components comprise mammalian cells and components of mammalian cells, further wherein the low density composition comprises the protein.

2. The method of claim 1 wherein the fluid comprising mammalian cells is a culture harvest from a bioreactor comprising cultured mammalian cells.

3. The method of claim 1 wherein the protein is an antibody or an antigen-binding fragment thereof.

4. The method of claim 3 wherein the antigen-binding fragment is a peptibody, an antibody derivative, an antibody analog, a fusion protein, a mutein, a bispecific protein or a multispecific protein.

5. The method of claim 3 wherein the antibody is a whole antibody, a single-chain variable fragment, a Fv, a Fab, a Fab', a F(ab')2, a diabody, a triabody, a tetrabody, a BiTE, a Fd, a dAb, a minibody, or a maxibody.

6. The method of claim 4 wherein the fusion protein comprises an antibody chain or an antigen-binding fragment thereof comprising light chain complementarity determining regions 1, 2 and 3 or heavy chain complementarity determining regions 1, 2 and 3.

7. The method of claim 4 wherein the fusion protein is a Chimeric Antigen Receptor (CAR).

8. The method of claim 1 wherein the protein is a granulocyte colony-stimulating factor, an erythropoiesis stimulating agent, a HER receptor, a cell adhesion molecule, a growth factor, an osteoinductive factor, insulin, a coagulation protein, a colony stimulating factor, a blood group antigen; a growth hormone, a growth hormone receptor, a T-cell receptor; a neurotrophic factor, a neurotrophin, a relaxin, an interferon, an interleukin, a viral antigen, a lipoprotein, an integrin, a rheumatoid factor, an immunotoxin, a surface-membrane protein, a transport protein, a homing receptor, an addressin, a regulatory protein, or an immunoadhesin.

9. The method of claim 1 further comprising subjecting the low density composition to a second centrifugation step performed in a disk-stack centrifuge.

10. The method of claim 1 further comprising subjecting the low density composition to a depth filtration step or a tangential flow filtration step.

11. The method of claim 1 further comprising subjecting the low density composition to any one or more of a second centrifugation step, a filtration step, an acoustic wave separation step, a flocculation step or a precipitation step.

12. A method for purifying a protein from a mammalian cell culture comprising:

(a) introducing a continuous stream of a cell culture fluid comprising mammalian cells into at least one decanter centrifuge;

(b) operating the decanter centrifuge, thereby separating fluid components into a low density fluid composition and a high density fluid composition;

(c) subjecting the low density fluid composition to depth filtration to yield a filtered low density fluid composition;

(d) recycling the filtered low density composition through the bioreactor to obtain a recycled low density composition;

(e) recycling the high density composition through the decanter centrifuge;

(f) contacting the recycled low density fluid composition with at least one chromatography medium; and (g) collecting fluid containing the protein from the chromatography medium, thereby purifying the protein.

13. The method of claim 12 further comprising subjecting the low density composition to any one or more of a second centrifugation step, a second filtration step, an acoustic wave separation step, a flocculation step or a precipitation step.

14. The method of claim 12 wherein the protein is an antibody, an antigen-binding fragment thereof, an antibody derivative, an antibody analog, a fusion protein, a peptibody, a mutein, a chimera, a bispecific protein or a multispecific protein.

15. The method of claim 14 wherein the antibody or antigen-binding fragment thereof is a single-chain variable fragment, a Fv, a Fab, a Fab', a F(ab')2, a diabody, a triabody, a tetrabody, a BiTE, a Fd, a dAb, a minibody, or a maxibody.

16. The method of claim 14 wherein the chimera comprises an antibody or antigen-binding fragment thereof.

17. The method of claim 14 wherein the chimera is a Chimeric Antigen Receptor.

* * * * *